United States Patent [19]

Havlice et al.

[11] 4,424,813

[45] Jan. 10, 1984

[54] MULTI-MODE ULTRASOUND SCANNER

[75] Inventors: James F. Havlice, Los Altos; Albert S. Waxman; Henry L. Schwartz, both of Los Gatos; David E. Stepner, Cupertino, all of Calif.

[73] Assignee: Diasonics, Inc., Milpitas, Calif.

[21] Appl. No.: 292,948

[22] Filed: Aug. 14, 1981

[51] Int. Cl.³ ............................................. G01N 29/04
[52] U.S. Cl. .................................................... 128/660
[58] Field of Search ................. 73/624, 625, 626, 628, 73/632, 641, 642; 128/660, 661, 662, 663

[56] References Cited

U.S. PATENT DOCUMENTS 4,094,306  6/1978  Kossoff .................................. 128/660
4,097,835  6/1978  Green .................................... 73/641
4,141,347  2/1979  Green et al. ........................... 73/627
4,246,791  1/1981  Glenn .................................... 128/660

*Primary Examiner*—William E. Kamm
*Assistant Examiner*—George Yanulis
*Attorney, Agent, or Firm*—Blakely, Sokoloff, Taylor & Zafman

[57] ABSTRACT

A multi-mode scanner head employing split (semicircular transducers) is described. In some modes such as simultaneous B-scan and M-scan each transducer moves independent of the other. For continuous Doppler mode the transducers move together. The relatively small, hand-held scanner head is particularly useful for cardiac examinations.

5 Claims, 10 Drawing Figures

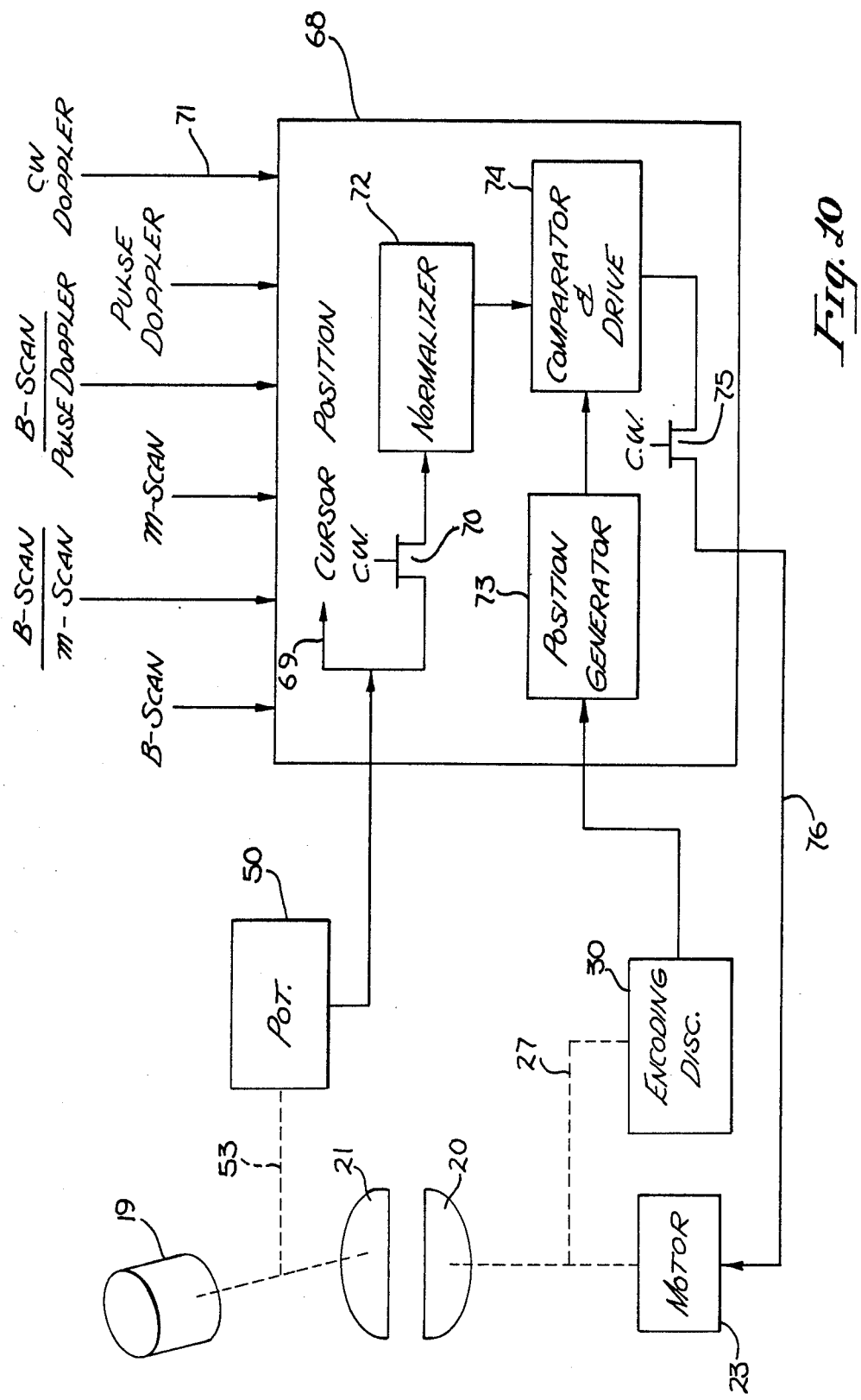

MULTI-MODE ULTRASOUND SCANNER

BACKGROUND OF THE INVENTION

1. Field of the Invention

The invention relates to the field of ultrasound imaging, particularly for medical applications.

2. Prior Art

In recent years, more emphasis has been placed on the use of ultrasound for medical diagnostics. Unlike x-rays which are known to be harmful, the levels of ultrasound energy used for diagnostics have been shown to be safe. In general, ultrasound scanners can be divided into two categories, those using phased arrays and those using separate transducers. The present invention relates to the latter category.

Scanners employing a plurality of transducers are used to provide continuous real time untrasound images. Such scanners are shown in U.S. Pat. No. 4,231,373 and U.S. Pat. No. 4,269,066.

The present invention uses a configuration of two transducers referred to as "split" transducers. Each transducer has a generally semicircular face; when the transducers are mounted their faces present a general circular shape. One advantage to this configuration is that the beams from both transducers are substantially coincident.

In the prior art, there are teachings for using split transducers for a continuous ultrasound Doppler examination. In this configuration, one transducer transmits a continuous ultrasound signal while the other transducer receives the echo. Crystal controlled filtering is used to sense the Doppler shift which is, by way of example, proportional to the velocity of blood flow. This Doppler technique is discussed in *Ultrasound and the Diagnosis of Cardiovascular-Pulmonary Disease* by Joyner, beginning at page 9, published by Yearbook Medical Publishers, Inc., 1974.

Applicant is aware of a research project where a split transducer configuration was used to provide a simultaneous B-scan and pulsed Doppler display. This prior art apparatus was a very large experimental unit, not susceptible to being hand-held. This experimental unit did not provide the wide range of operating modes described in this application. The short fluid path between the transducers used in the present invention and the patient were not employed, making the unit impractical for many types of examinations, such as complete cardiac examinations.

As will be seen, the present invention provides a scanning apparatus employing a split transducer. The apparatus can be used in a plurality of modes and combination of modes, such as B-scan, M-scan, pulsed Doppler and continuous Doppler. The apparatus is small and easily hand-held, allowing it to be used for cardiac examinations in addition to other examinations.

SUMMARY OF THE INVENTION

An ultrasound medical scanning apparatus is described which is hand-holdable and thus easily positioned during an examination. A pair of ultrasound tranducers, each having a generally semicircular face, are mounted for independent pivotal movement within a housing about a common axis. This axis is generally perpendicular to the chords of the semicircular faces of the transducers. A motor is coupled to one of the transducers for causing the transducer, by way of example, to move in oscillatory movement. A first position detection means coupled to this transducer, which includes a disc, provides signals which permit the position of the transducr to be determined. A manual positioning means (knob) is used for manually positioning the other transducer. A second position detection means which includes a potentiometer, is coupled to the other transducer for providing signals representative of the position of this transducer. The transducers are mounted within a fluid chamber; a membrane defines one end of the chamber. During certain modes of operation, such as simultaneous B-scan and M-scan, the transducers are moved independently. During other modes of operation, such as continuous Doppler, the transducers are moved together under control of the manual positioning means. The scanning apparatus can be used to provide data for a number of different scans or modes.

BRIEF DESCRIPTION OF THE DRAWINGS

FIGS. 7–10 are used primarily to illustrate the manual positioning mechanism used to pivot one of the transducers.

DETAILED DESCRIPTION OF THE INVENTION

A multi-mode scanning apparatus (scanning head) is described. In the following description, numerous specific details are set forth such as specific frequencies and pulse rates in order to provide a thorough understanding of the present invention. However, it will be obvious to one skilled in the art that the invention may be practiced without these specific details. In other instances, well-known structures and electrical processing means have not been described in detail in order not to obscure the present invention in unnecessary detail.

Figure 1:
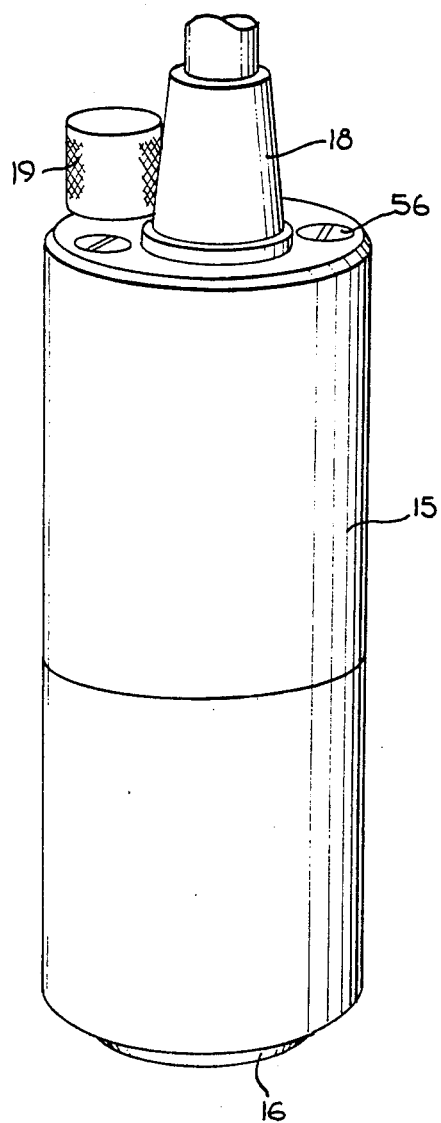
FIG. 1 is a perspective view showing the overall shape of the invented scanning apparatus.
Figure 2:
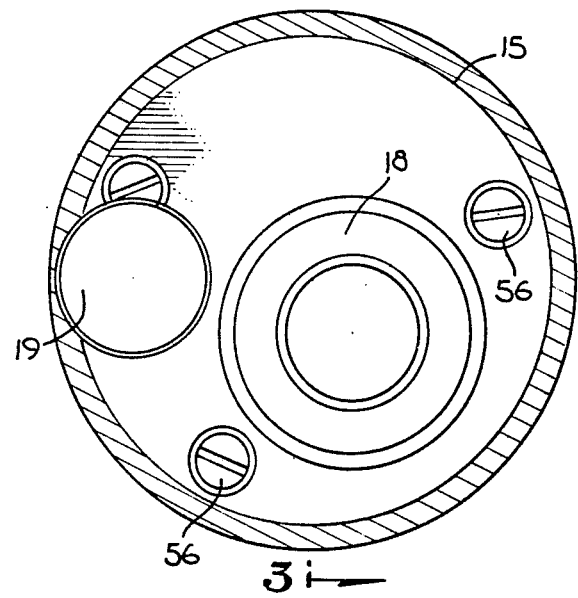
FIG. 2 is a top view of the apparatus of FIG. 1.

Referring briefly to FIGS. 1 and 2, the scanning apparatus or head is a generally cylindrically shaped unit which in the presently preferred embodiment is approximately 1¾ inches in diameter and approximately 6 inches in length. Thus, the scanning head is readily hand-holdable. One end includes a boot or membrane 16 which is brought in contact with the body for examinations. The other end comprises a generally cylindrical housing 15, the end of which includes a knob 19, connector 18 and screws 56. The electrical connector 18 connects the scanning head with the electrical processing unit which typically incorporates a CRT display. Knob 19 is used to manually position one of the transducers of the scanning head.

As will be described in more detail, the scanning head may be used to provide data for a B-scan display, simultaneous B-scan and pulsed Doppler display, M-scan display, simultaneous B-scan and M-scan display, and a continuous (CW) Doppler display.

Figure 3:
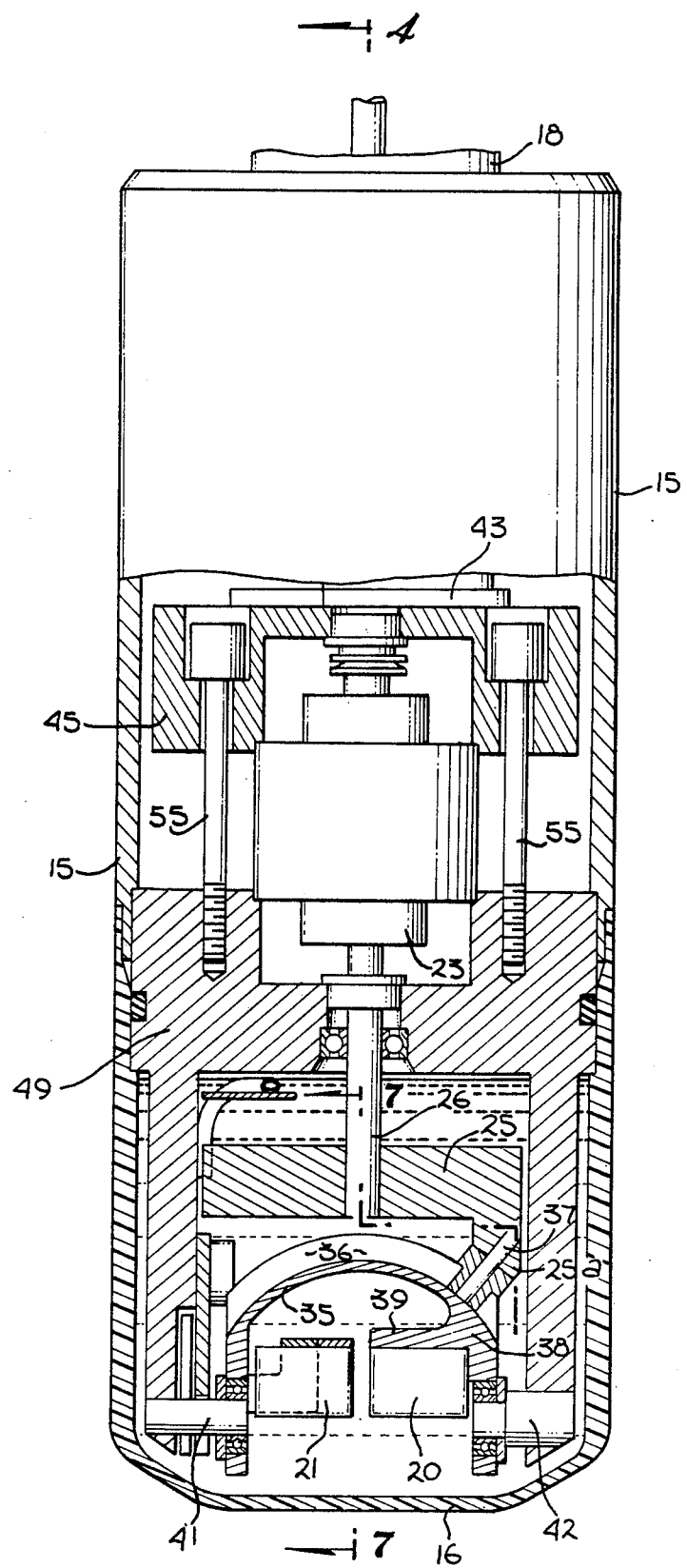
FIG. 3 is a partial cross-sectional elevation view of the apparatus of FIGS. 1 and 2, generally taken through section line 3—3 of FIG. 2.

Referring now to FIG. 3, the scanning head includes a pair of transducers 20 and 21. Each transducer has a semicircular face (see FIG. 9); the tranducers are mounted such that their combined faces form an approximate circle. The transducers are mounted for independent pivotal movement about a common axis which includes the pins 41 and 42. This axis is generally perpendicular to the chords of the semicircular transducer faces. Commercially available transducers are used for transducers 20 and 21.

Transducer 20, as will be described, is moved in oscillatory movement by motor 23 when providing B-scan data. In the presently preferred embodiment, this transducer operates at a center frequency of approximately 3.5 mHz and at a pulse rate of approximately 5 kHz. The angular position of the transducer 21 is manually selected through the knob 19 of FIG. 1. This transducer provides data for the M-scan and Doppler modes. By way of example, during the M-scan mode, this transducer operates at a frequency of approximately 3.5 mHz with pulses occurring at a rate of approximately 800 Hz. During the CW Doppler mode, the transducers move together under the control of the knob 19. This mode of operation will be discussed in greater detail in conjunction with FIG. 10.

Figure 6:
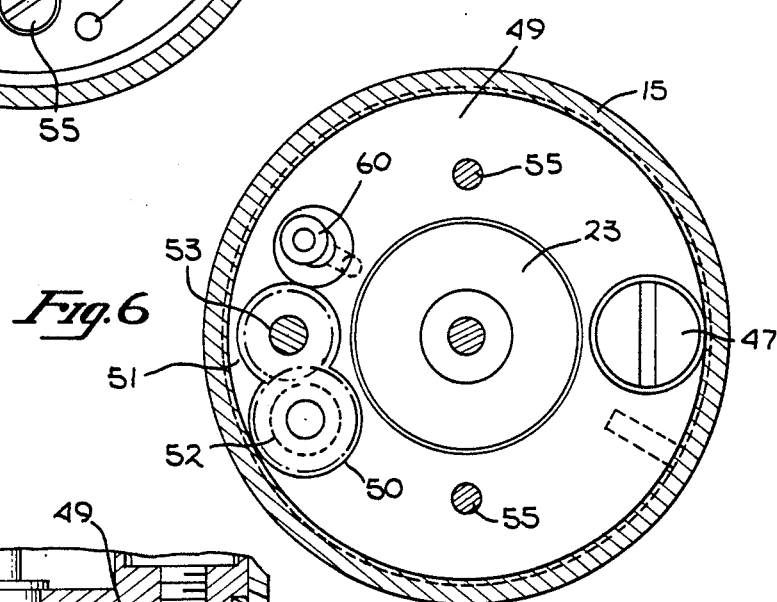
FIG. 6 is a cross-sectional plan view of the invented apparatus taken through section line 6—6 of FIG. 4.
Figure 7:
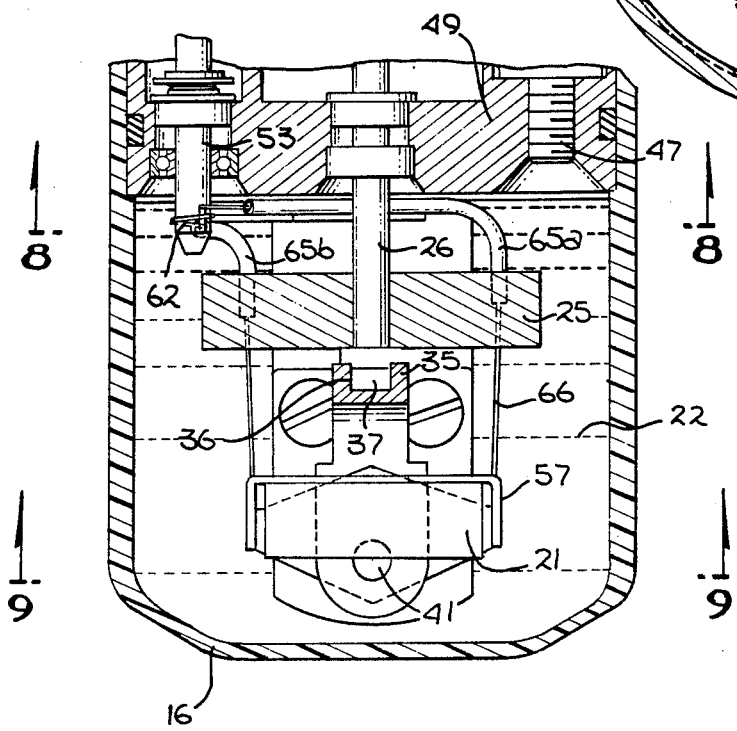
FIG. 7 is a partial cross-sectional elevation view of the invented apparatus generally taken through section line 7—7 of FIG. 3.

A fluid chamber 22 (See FIG. 7) is defined within the scanning head. The membrane 16 defines a portion of this chamber. The various shafts and wires entering this fluid chamber (such as shafts 26 and 53) include appropriate seals to retain the fluid within the chamber. The plug 47 shown in FIGS. 6 and 7 is used to fill the chamber; an expansion nipple 60 is included on the lower support member 49. The interior of the fluid chamber is lined with rubber (not shown) to reduce reverberations within the chamber.

In the presently preferred embodiment, the membrane comprises a low density polyethelene approximately 0.040 inches thick. The fluid for the chamber is selected such that the velocity of ultrasound in the fluid approximately equals the velocity of ultrasound in the body. Presently castor oil is used.

The direct current motor 23 is mounted between the lower support member 49 and a central support member 45 as best seen in FIGS. 3, 4, 5, and 6. The screws 55 secure these two support members to each other. The screws 56 of FIG. 1 secure the exterior housing 15 and its upper plate to the support member 45.

Figure 4:
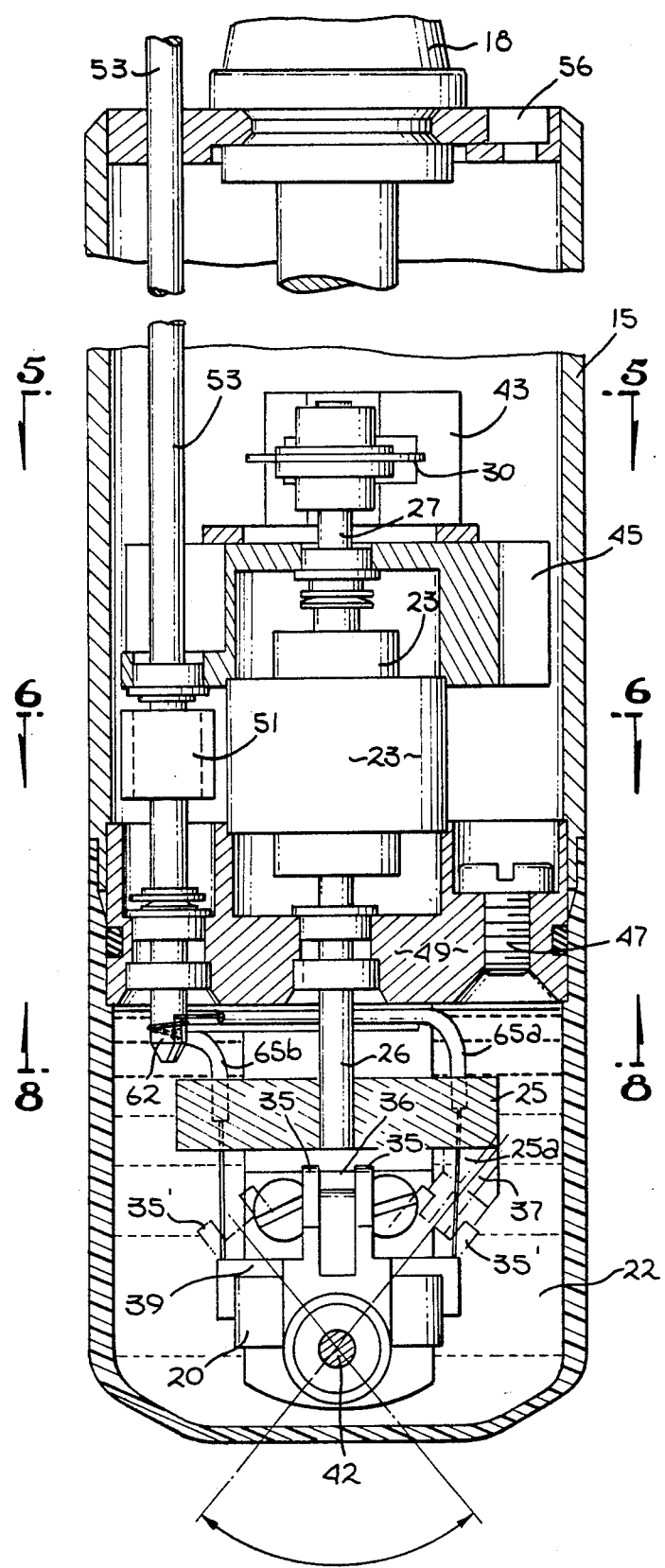
FIG. 4 is a cross-sectional elevation view of the apparatus of FIGS. 1-3, generally taken through the staggered section line 4—4 of FIG. 3.

The rotor shaft of motor 23 extends in both directions from the motor 23. In one direction, as best seen in FIG. 4, the shaft 27 drives a disc 30. In the other direction, the shaft 26 drives a flywheel 25. As will be discussed, a unique mechanism is used to convert the rotation of this flywheel to oscillatory motion for the transducer 20.

Figure 5:
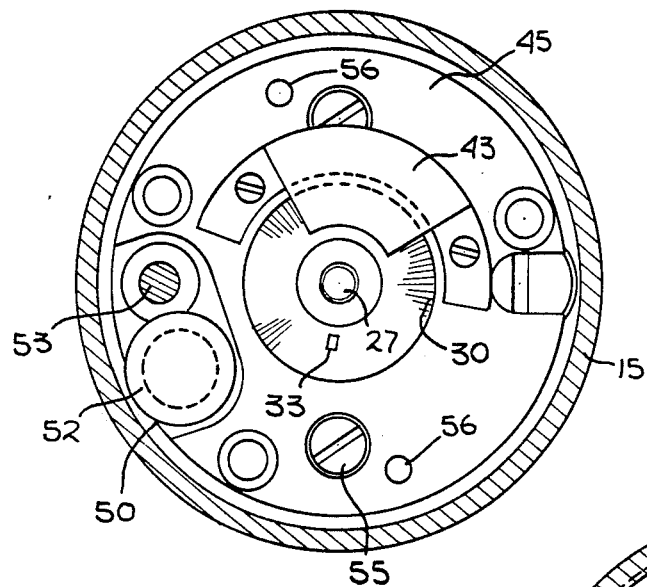
FIG. 5 is a cross-sectional plan view of the invented apparatus taken through section line 5—5 of FIG. 4.

As best seen in FIG. 5, the disc 30 includes a plurality of evenly disposed radial slots 31 cut through the disk near its periphery, and an inner single slot 33. Photoelectric detectors are included within the assembly 43 along with light emitting diodes to sense the rotation of the disc. A pair of detectors are used to sense the leading edge and trailing edge of the slots 31. By sensing the leading and trailing edges of the slots, the direction of rotation can be determined. The slot 33 provides position information. (The use of a pair of detectors to detect the leading edge and trailing edge of the slots is known in the art.) The electrical signals from the detectors included within the assembly 43 permit the position of the disc 30 (and transducer 20) to be determined.

The mechanism for driving the transducer 20 in its oscillatory movement is best seen in FIGS. 3 and 4. It should be noted that the view of FIG. 4 is a staggered view; in the region of transducer 20 this view is taken to the right of the transducer 20 and rocker 39 as viewed from FIG. 3. The rocker 39 includes a curved upper section 35 which interconnects the rocker ends. These ends are mounted to bearings at pins 41 and 42. The rocker defines a cradle-like region into which the transducer 20 is affixed. A slot 36 is defined by rocker 39 between the edges of the curved section 35. An eccentric pin 37 and a wear sleeve 38 extend from the flywheel 25 (FIG. 3) and cooperatively engage the slot 36. As the flywheel rotates, the pin and sleeve 38 drive the rocker 39 and hence transducer 20 in oscillatory motion, several positions of this motion being shown by 35' in FIG. 4.

As presently implemented, the pin 37 is secured to the flywheel 25 from a downwardly extending portion 25a of the flywheel. The pin 37 in one direction extends through the axis about which transducer 20 oscillates. In the other direction, the projection of the pin does not intersect the main body of flywheel 25. By using the additional portion 25a of the flywheel, the pin 37 can be slanted at a greater angle relative to the vertical. This larger angle can also be obtained by making the flywheel larger in diameter, however, this is not practical for a hand-held unit. By increasing the angle of the pin 37, the number of degrees through which the transducer 20 oscillates is increased. Note that if the pin were to extend directly from the main body of the flywheel 25, the swing of the transducer would be decreased.

Referring to FIG. 3, the transducer 21 is secured to a support 57 which pivots about pin 41. As mentioned, transducer 21 moves independently of transducer 20. The position of transducer 21 is controlled by the knob 19 of FIG. 1; this knob is secured to a shaft 53 which terminates in a capstan 62 shown in FIGS. 4 and 7. A gear 51 best seen in FIG. 6 is secured along shaft 53 and cooperatively engages gear 52. The gear 52 drives a potentiometer 50. A voltage from this potentiometer provides a signal representative of the position of the shaft and transducer 21.

Figure 8:
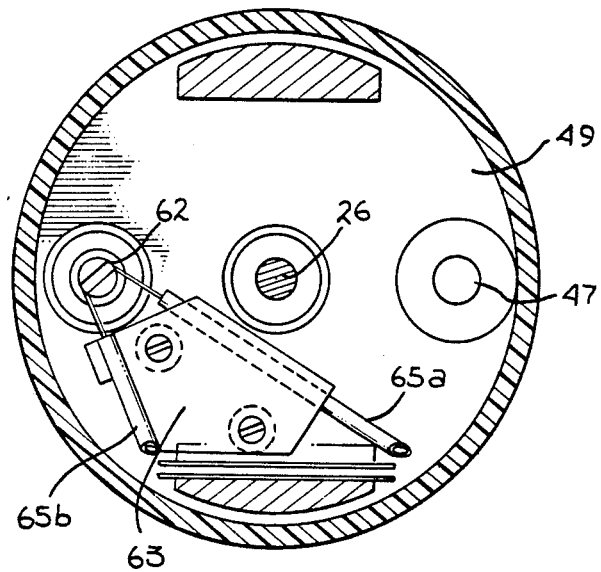
FIG. 8 is a cross-sectional (bottom) view of the invented apparatus generally taken through section line 8—8 of FIG. 7.
Figure 9:
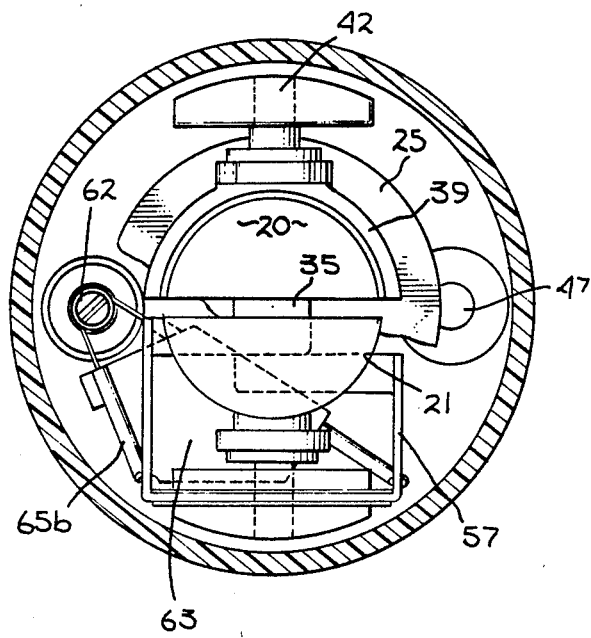
FIG. 9 is a cross-sectional (bottom) view of the invented apparatus generally taken through section line 9—9 of FIG. 7.

In FIGS. 7, 8 and 9 the mechanism for converting the rotational movement of the shaft 53 to angular movement of the transducer 21 is illustrated. A wire rope 66 engages the capstan 62 and is directed through the tubes 65a and 65b from a generally horizontal direction to a vertical direction. The ends of this wire rope are coupled to the support 57 on opposite sides of pin 41. (Each of the tubes 65a and 65b include right angle bends best seen in FIG. 7.) The stainles steel tubes 65a and 65b are braised to a support 63 which is secured to the lower support member 49. As shaft 53 rotates, the angle of the transducer 21 is varied as indicated by the dotted lines in FIG. 7.

Well-known circuit means are used to process the electrical signals from the transducers 20 and 21 to provide the B-scan, M-scan, pulsed Doppler and continuous Doppler displays. Display circuitry and signal processing techniques for ultrasound displays are described in U.S. Pat. No. 4,241,412. Circuit techniques for providing simultaneous B-scan and pulsed Doppler displays which are also applicable to simultaneous B-scan and M-scan displays are described in copending application Ser. No. 257,506 filed on Apr. 24, 1981, now U.S. Pat. No. 4,407,293, entitled "Ultrasound Imaging Apparatus for Providing Simultaneous B-Scan and Doppler Data" and assigned to the assignee of the present invention.

During the B-scan mode, the potential from the potentiometer 50 is used to display a cursor or line on the B-scan display. For example, during a B-scan display, the potential from the potentiometer 50 along with a range gate signal are used to position a cursor. This cursor shows the region from which the pulse Doppler echoes are to be sensed. Similarly, markers can be set on the B-scan display to establish projections for M-scan or continuous Doppler displays. For the present invention, the potential from potentiometer 50 is also used to position transducer 20 for the CW Doppler mode as will be described.

During the CW Doppler mode, it is necessary that transducers 20 and 21 move together. One transducer transmits a continuous signal at a precisely controlled frequency while the other receives the echos. Mechanical means may be used to lock transducers 20 and 21 so that they move in unison under the control of knob 19, however, as presently preferred, a servomechanism loop is employed.

Referring to FIG. 10, a portion 68 of an electrical control unit used in conjunction with the scanning head is illustrated. The transducers 20 and 21 are also illustrated. The knob 19 along with the potentiometer 50 are shown coupled through a representation of the shaft 53. Similarly, transducer 20 is shown coupled by a representation of shaft 27 to the motor 23 and encoding disc 30. A potential from the potentiometer 50 is coupled to the control unit 68. Similarly, the signals from the encoding disc are coupled to a position generator 73 of unit 68. The position generator 73 generates a signal representative of the position of the transducer 20 based on the signals from disc 30.

The several operator selected modes such as B-scan, simultaneous B-scan and M-scan, etc., are shown as inputs to unit 68. When the CW Doppler mode is selected, a signal is present on line 71. This signal closes a switch 70 and couples the potentiometer signal 50 to a normalizer 72. The potential from potentiometer 50 is normalized so that it is compatible with the potential from generator 73. The potential from normalizer 72 and generator 73 are compared and a error signal is generated through the comparator and drive means 74. The error signal is coupled through switch 75 and used to drive motor 23. In this manner the motor 23 positions the transducer 20 such that it is in alignment with transducer 21. That is, as transducer 21 is manually moved, the motor drives transducer 20 so that the faces of the two transducers remain coplanar. The particular circuits used to cause the transducers to move together is not significant and any one of a plurality of well-known servo loops may be employed.

Thus, a scanning apparatus or head has been described employing a split transducer. The described scanning head can be used in multiple modes including a CW Doppler mode. The described device is particularly useful for cardiac examinations.

We claim:

1. An ultrasound medical scanning apparatus comprising:
   a hand-holdable housing;
   a pair of ultrasound transducers having faces together shaped to generally form a circle, said transducers mounted for independent pivotal movement within said housing about a common axis;
   a motor;
   coupling means for coupling one of said transducers to said motor for pivoting said transducer in oscillating motion about said axis comprising:
   a flywheel driven by said motor;
   an eccentrically mounted pin extending from said flywheel;
   a pivotally mounted rocker member to which said one transducer is affixed, said member including a curved slot; said pin cooperatively engaging said slot so as to convert the rotational movement of said flywheel into said oscillatory movement;
   first position detection means coupled to said one transducer for providing signals representative of the position of said one transducer, said first detection means being disposed within said housing;
   manual positioning means for manually pivoting the other of said transducers about said axis;
   second position detection means coupled to said other transducer for providing signals representative of the position of said other transducer, said second detection means being disposed within said housing;
   a fluid chamber within said housing enclosing said transducers; and,
   a membrane for contacting a body defining a part of said chamber such that ultrasound from said transducers passes through said membrane into the body,
   whereby a multi-mode, hand-holdable ultrasound apparatus is realized.

2. The apparatus defind by claim 1 wherein said pin is mounted on a protrusion of said flywheel such that a projection of said pin does not intersect the body of said flywheel, whereby said one transducer oscillates through a larger angle.

3. The apparatus defined by claim 1 including means for selectively causing said transducers to pivot together.

4. The apparatus defined by claim 3 wherein said tranducers pivot together under control of said manual positioning means.

5. The apparatus defined by claim 4 wherein said motor is controlled by said first and second detection means when said transducers pivot together.

* * * * *